United States Patent
Vitella et al.

(10) Patent No.: US 10,422,730 B2
(45) Date of Patent: Sep. 24, 2019

(54) LIQUID INLET DEVICE

(71) Applicant: Horizon Technology, Inc., Salem, NH (US)

(72) Inventors: Thomas James Vitella, Salem, NH (US); Robert Stockton Johnson, Hampstead, NH (US)

(73) Assignee: Horizon Technology, Inc., Salem, NH (US)

( * ) Notice: Subject to any disclaimer, the term of this patent is extended or adjusted under 35 U.S.C. 154(b) by 173 days.

(21) Appl. No.: 15/700,934

(22) Filed: Sep. 11, 2017

(65) Prior Publication Data

US 2018/0073965 A1    Mar. 15, 2018

Related U.S. Application Data

(60) Provisional application No. 62/393,562, filed on Sep. 12, 2016.

(51) Int. Cl.
*G01N 1/40* (2006.01)
*B01D 47/06* (2006.01)
*B01L 3/00* (2006.01)
*B01L 3/02* (2006.01)

(52) U.S. Cl.
CPC ............. *G01N 1/405* (2013.01); *B01D 47/06* (2013.01); *B01L 3/0265* (2013.01); *B01L 3/56* (2013.01); *B01L 2200/026* (2013.01); *B01L 2200/0689* (2013.01); *B01L 2400/0616* (2013.01)

(58) Field of Classification Search
CPC ....... B01L 2200/026; B01L 2200/0689; B01L 2400/0616; B01L 3/0265; B01L 3/56; G01N 1/405
See application file for complete search history.

(56) References Cited

U.S. PATENT DOCUMENTS

2011/0159596 A1* 6/2011 Keinan ................ G01N 1/2211
                                                                436/52
2014/0182457 A1* 7/2014 Rana ...................... B01D 53/18
                                                                96/245

* cited by examiner

*Primary Examiner* — Jennifer Wecker
(74) *Attorney, Agent, or Firm* — Hamilton, Brook, Smith & Reynolds, P.C.

(57) ABSTRACT

Described is a liquid inlet valve having a housing configured to receive the opening of a sample bottle, a valve, a nozzle positioned within the housing, and a tube that extends downwardly from the housing. The liquid inlet valve is useful for transferring liquid samples from a sample bottle to a solvent phase extraction (SPE) disk of a bottle extractor system for purposes of conducting environmental analysis.

13 Claims, 10 Drawing Sheets

LIQUID INLET DEVICE

RELATED APPLICATION

This application claims the benefit of U.S. Provisional Application No. 62/393,562, filed on Sep. 12, 2016. The entire teachings of the above application are incorporated herein by reference.

BACKGROUND

Liquid samples are often collected and transported to a laboratory for purposes of conducting environmental analysis of the sample. Frequently, liquid samples are collected in a standardized container, such as a one liter glass sample bottle having a threaded top. Examples of apparatuses for use in testing liquid samples are described in U.S. Pat. Nos. 5,753,105 and 6,027,638.

One extraction technique is to filter the sample through a solid phase extraction (SPE) disk. As the sample filters through the SPE disk, the media within the SPE disk removes and concentrates the analytes of interest. Prior to testing, however, the SPE disk must be conditioned with a small volume of solvent. During processing, the sample bottle must be rinsed with solvent to ensure that potential analytes do not remain attached to the glass surface of the sample bottle, but are instead transferred to the disk. Improved devices and methods for facilitating preconditioning of the disk, transfer of the liquid sample onto the disk, and rinsing of the sample bottle would improve testing throughput by reducing the amount of manual labor necessary to extract a sample.

SUMMARY OF THE INVENTION

Described herein is a liquid inlet device. The device includes a housing configured to receive an opening of a sample bottle, a valve, a nozzle positioned within the housing, and a tube that extends downwardly from the housing. The nozzle has an inlet and an outlet, with the inlet coupled to a port of the housing. The liquid inlet device is configured so that when the valve is closed, solvent sprays through the nozzle, against the valve, and through the tube, and so that when the valve is opened, solvent sprays through the nozzle, through the valve to rinse the sample bottle, back through the valve, and through the tube. The valve can be a ball valve or a plug valve. The ball valve or the plug valve can have a rotatable seal that couples with an actuator. The seal can have a stem, which is typically adapted for manipulation by an actuator. The valve can include a flange portion that ensures a tight fit between the valve and a seat for the valve. A constant force spring and a spanner nut can secure the valve to the housing. In some embodiments, the housing can have a threaded portion configured to receive the opening of the sample bottle. A first insert can be positioned within the housing, the first insert having the threaded portion configured to receive the opening of the sample bottle. In some embodiments, a second insert is positioned within the housing, the second insert receiving the nozzle and the tube. The nozzle can be rotatably adjustable, and the inlet of the nozzle is oriented at 180° relative to the outlet of the nozzle.

Also described herein is a method of extracting a sample from a sample bottle. The method includes coupling a liquid inlet device, such as those described in the preceding paragraph, to the sample bottle. The liquid inlet device and sample bottle are positioned so the tube extends towards a chamber, the port receives pressurized solvent, and valve receives an actuator. Solvent is sprayed through the nozzle with the valve in a closed position so that solvent sprays through the nozzle, against the valve, and through the tube to contact a disk. The valve is opened so that a sample in the sample bottle pass through the tube and contacts the disk. Solvent is sprayed through the nozzle with the valve in an open position so that solvent sprays through the valve to rinse the sample bottle, back through the device, and through the tube. Typically, the sample is aqueous and the solvent is an organic solvent. In some instances, liquid inlet device and sample bottle are inverted so that the sample bottle is upside down prior to step positioning the liquid inlet device and sample bottle so the tube extends towards a chamber, the port receives pressurized solvent, and valve receives an actuator.

The liquid inlet device and methods of extracting a sample provide improvements over prior liquid handling devices and methods for environmental analysis. The liquid inlet device is removably attachable to a sample bottle, and can be attached to a sample bottle while the bottle is in an upright position, thereby minimizing the risk of accidentally spilling a sample. The liquid inlet device has a threaded portion that is configured to couple the liquid inlet device to standard sample bottles used in environmental analysis. Using different cap adapters, allows sample bottles with various thread patterns to be used. Significantly, the liquid inlet device is configured to provide a solvent spray to rinse a sample bottle, and it can also dispense solvent through a downward-facing tube onto an SPE disk, thereby eliminating the need for separate valves and solvent lines for dispensing onto the disk.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Described herein with reference to FIGS. 1-6 is a liquid inlet device 100. The liquid inlet device 100 may be used as a water inlet device even though it is suitable for use with a wide variety of liquids. The liquid inlet device 100 has a housing 110, which is typically formed of a polymer. Near the top of housing 110 is first insert 120, which includes a threaded opening 120a that is adapted for coupling with a threaded portion 210 of sample bottle 200 (see FIG. 6). Preferably, a pliable, chemically inert gasket 125 (see FIG. 4) is positioned at the interface between liquid inlet device 100 and sample bottle 200 in order to ensure a tight seal. While the embodiment illustrated has a threaded opening 120a adapted for coupling with a threaded portion 210 of a sample bottle 200, other sealing mechanisms for coupling the housing 110 with the sample bottle 200 are suitable. For example, a press-fit arrangement between housing 110 and sample bottle 200 is suitable.

Near the bottom of housing 110 is second insert 135 that couples the housing 110 to a downwardly extending tube 130, which is referred to as "the downtube." Second insert 135 includes opening 160, through which is inserted a rotatably adjustable nozzle 165, referred to as a spray nozzle. Nozzle 165 can be press-fit into housing 110, either by hand or with the aid of a flat blade screwdriver. Screws 122 are employed where indicated to couple the components together. The particular embodiment illustrated includes first insert 120 and second insert 135 within housing 110, although the housing 110 can be molded appropriately such that inserts are not required.

Figure 5:
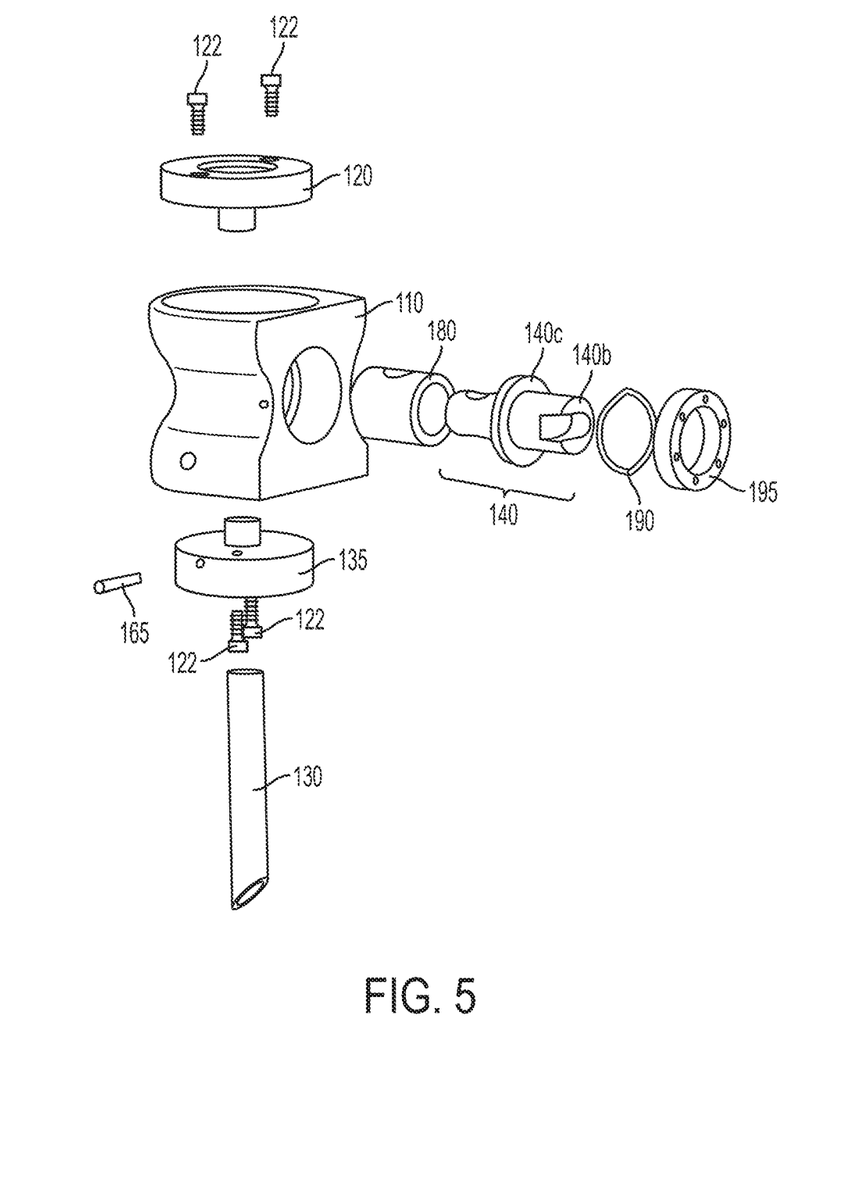
FIG. 5 is an exploded view of the liquid inlet device.

Housing 110 supports and encloses seat 180 (FIG. 5). Valve seal 140 extends outwardly from the housing 110 and has a plug portion 140a that fits within seat 180. Together, seat 180 and plug portion 140a function as a plug valve. Alternatively, valve seal 140 can have a ball portion rather than a plug portion 140a, in which case the ball portion and seat 180 function as a ball valve. While the particular embodiment illustrated is a plug valve, other types of valves are also suitable, such as a ball valve or a spool valve. Valve seal 140 has a stem portion 140b, which is typically adapted for manipulation by an actuator (not shown) of bottle extractor system 300 (FIG. 7D). Rotation of stem 140b causes plug portion 140a (or ball portion) to rotate, thereby controlling liquid flow through the liquid inlet device 100. Constant force spring 190 and externally threaded spanner nut 195 are adapted for securing the valve seal 140 to the housing 110, and cylindrical flange portion 140c ensures a tight fit between valve seal 140 and seat 180.

Figure 1:
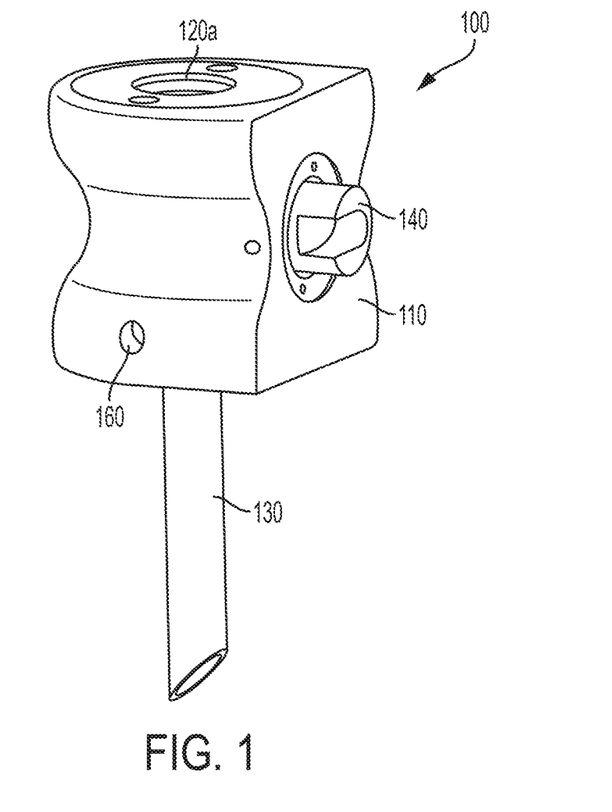
FIG. 1 is a perspective view a liquid inlet device.
Figure 2:
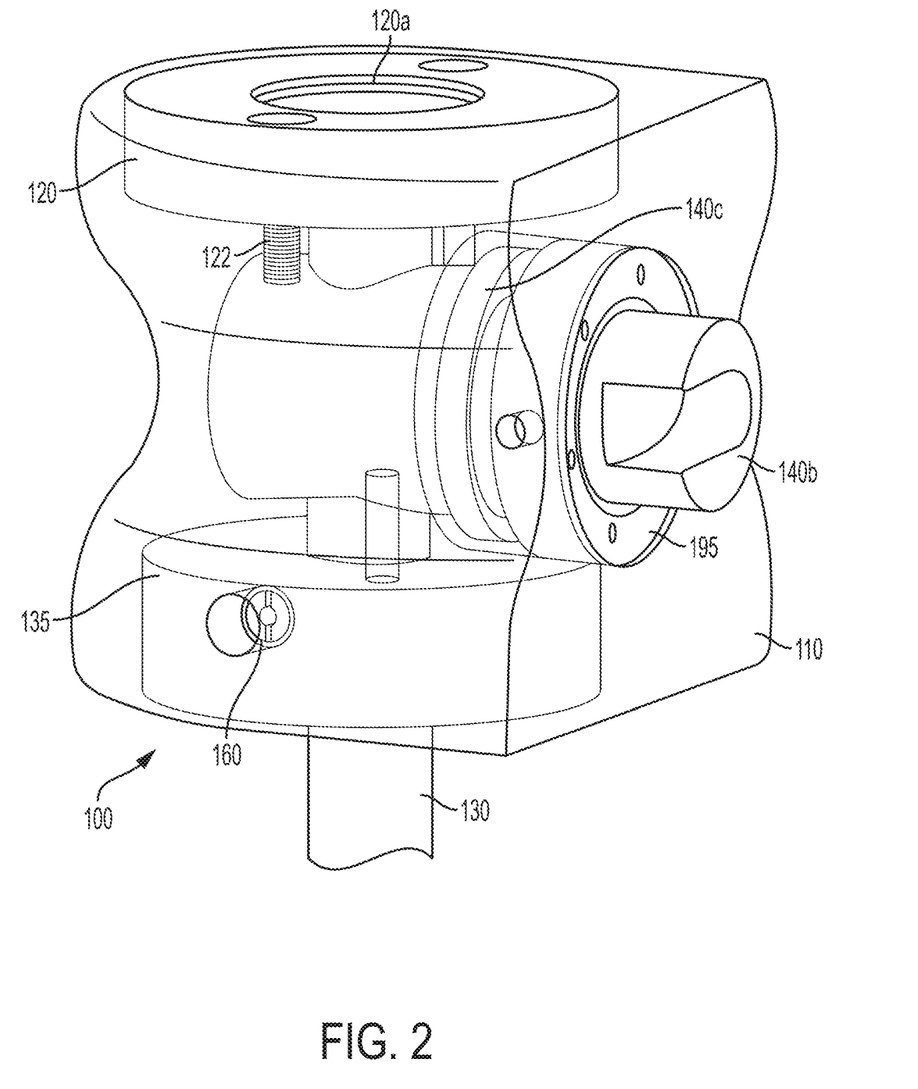
FIG. 2 is the liquid inlet device with the housing in phantom.
Figure 3:
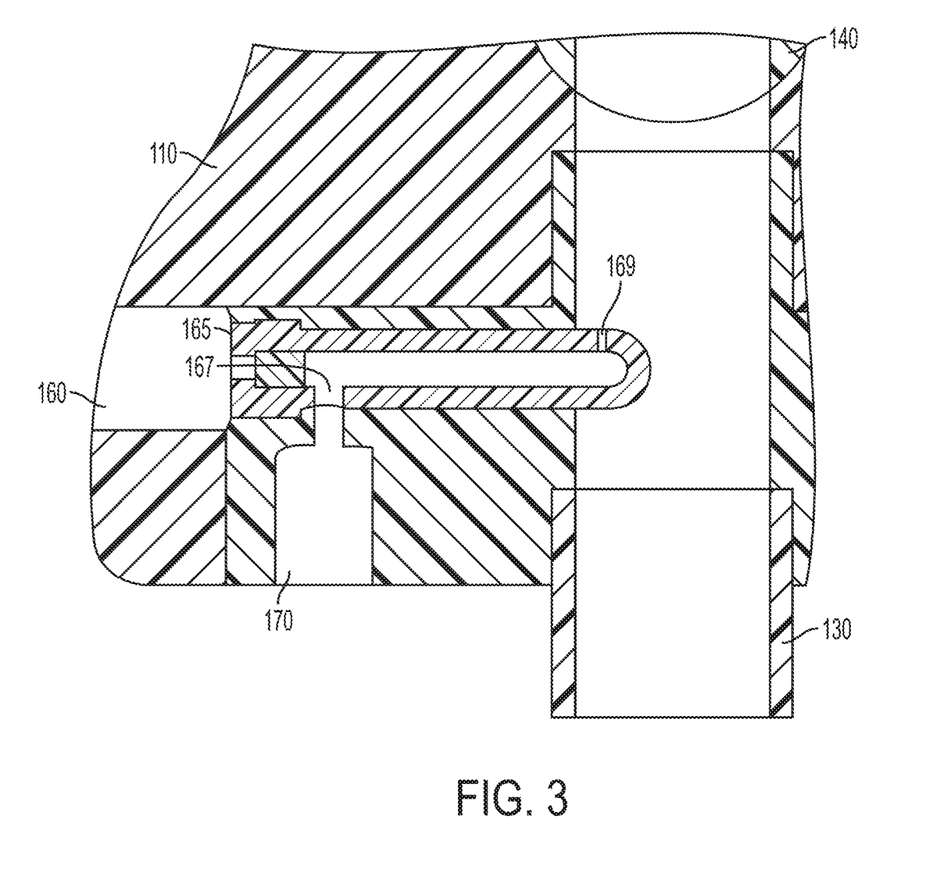
FIG. 3 is a magnified view of a portion of the liquid inlet device.
Figure 4:
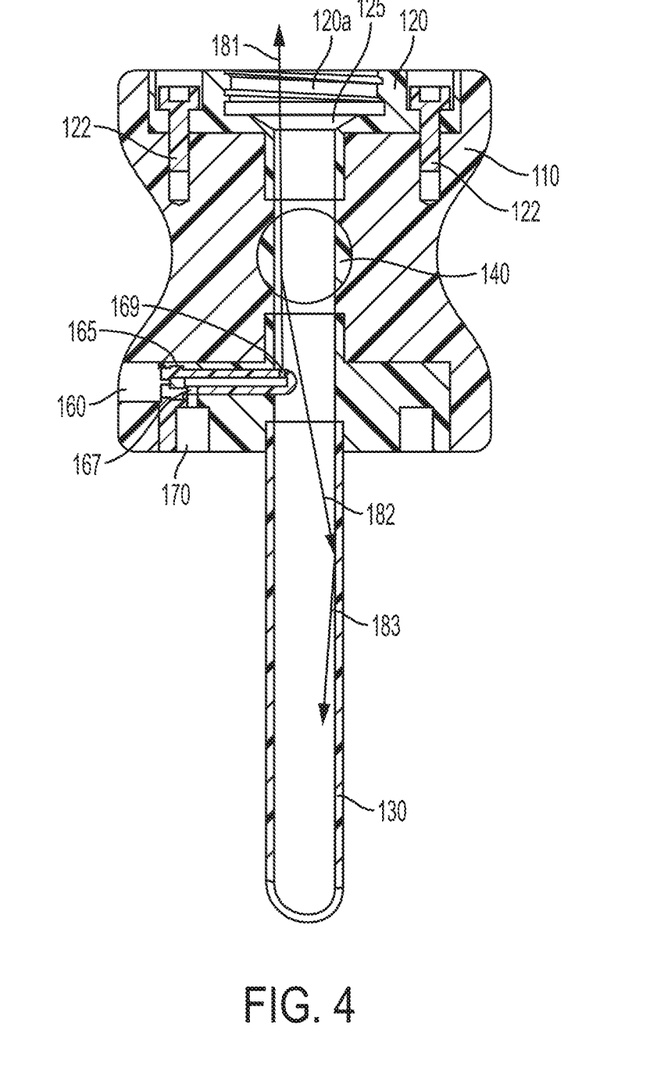
FIG. 4 is cross-sectional view of the liquid inlet device illustrating flow of a liquid through the device.
Figure 6:
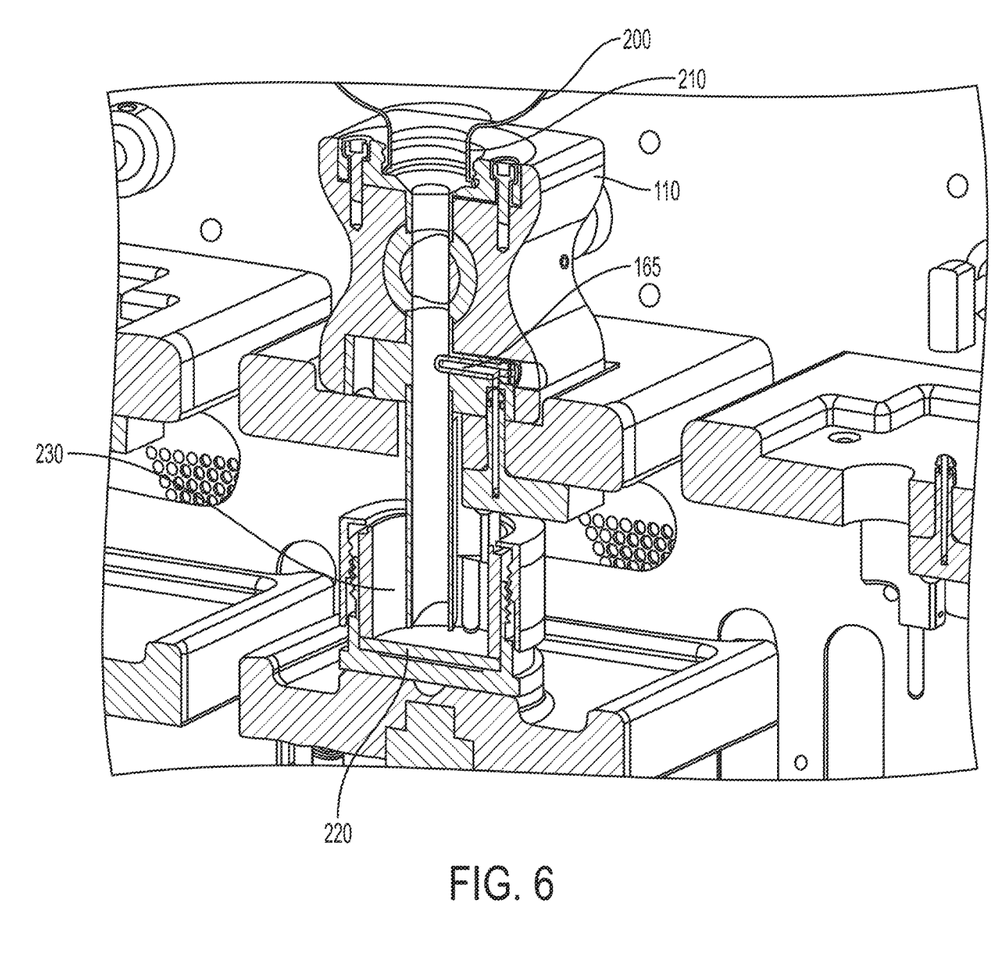
FIG. 6 is a cross-sectional view of the liquid inlet device coupled to a sample bottle and mounted in a bottle extractor system.

An important feature of liquid inlet device 100 is that a liquid, such as a solvent, can be reflected through downwardly extending tube 130, and can also be sprayed upwardly into sample bottle 200, as illustrated in FIG. 4. Pressurized liquid enters through port 170 of housing 110, passes through inlet 167 of nozzle 165, and exits through outlet 169 of nozzle 165. When valve seal 140 is in a closed position, liquid sprays upwardly through outlet 169 of nozzle, but then contacts the closed plug portion 140a, or alternatively ball portion, and falls downwardly due to gravitational forces, as indicated by arrows 182 and 183. Ultimately, the liquid contacts SPE disk 220 in the bottle extractor system (FIG. 6). Prior to using the bottle extractor system, solvent is dispensed onto disk 220 to condition the disk 220 for sample analysis. Then, the solvent is turned off, and valve seal 140 is turned, preferably by an actuator of the bottle extractor system 300, to the open position. Liquid in sample bottle 200 passes through the downwardly extending tube 130 to contact disk 220. When the liquid sample has completely drained from the sample bottle, and with valve seal 140 in an open position, a liquid solvent can spray upwardly through outlet 169 of nozzle and flow into sample bottle 200, as indicated by arrow 181. The liquid rinses sample bottle 200 and flows back down water inlet device 100 and into chamber 230. Other types of valves, such as a spool valve, are also suitable. When the valve 140 is in a closed position, solvent sprays through the nozzle 165 against the bottom side of the valve 140, and drains down through the tube 130. When valve 140 is in an opened position, solvent sprays through the nozzle 165, through the valve 140 to rinse the sample bottle 200, back through the valve 140, and down through the tube 130. As illustrated, inlet 167 of nozzle 165 is oriented at 180° relative to outlet 169 of nozzle 165. Inlet 167 is also offset from outlet 169. The illustrated arrangement of inlet 167 and outlet 169 ensures the solvent spray will contact the bottom of the sample bottle, and effectively rinse the sample bottle. Spraying solvent into sample bottle 200 permits the sample bottle to be rinsed without requiring removal of the sample bottle from the testing apparatus. United States Environmental Protection Agency (EPA) protocols currently require rinsing of sample bottles, so a device that permits the sample bottle to be rinsed without requiring removal of the sample bottle from the testing apparatus increases testing throughput. Thus, the liquid inlet device facilitates conditioning of the disk with solvent and rinsing the sample bottle with solvent, all without requiring removal of the liquid inlet device 100 from the sample bottle 200.

Figure 7A:
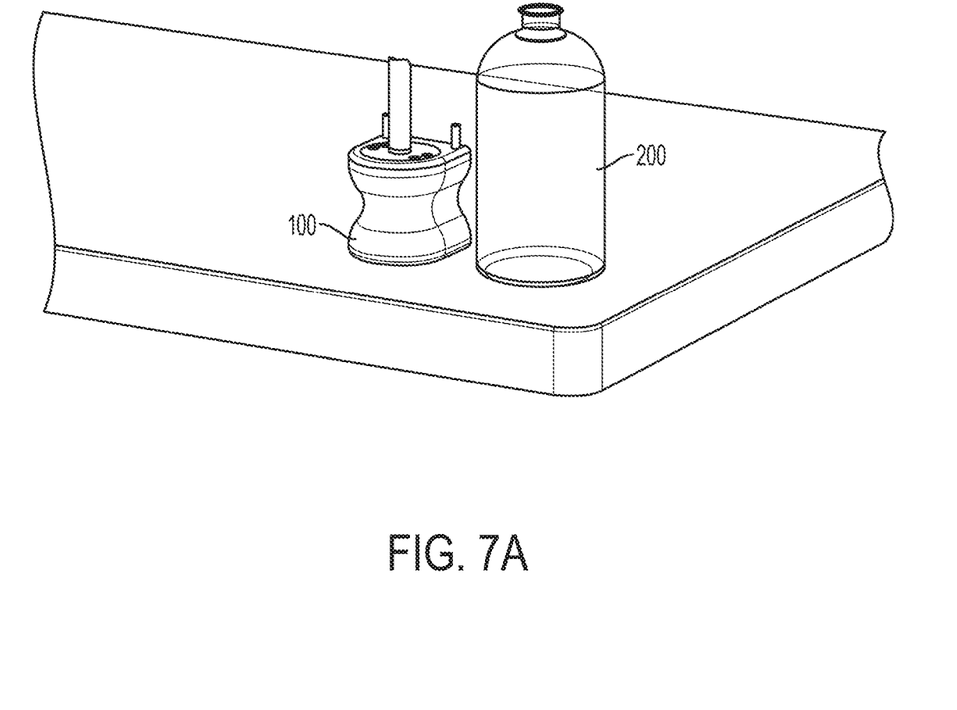
FIGS. 7A-D are a series of schematics illustrating use of the liquid inlet device.
Figure 7B:
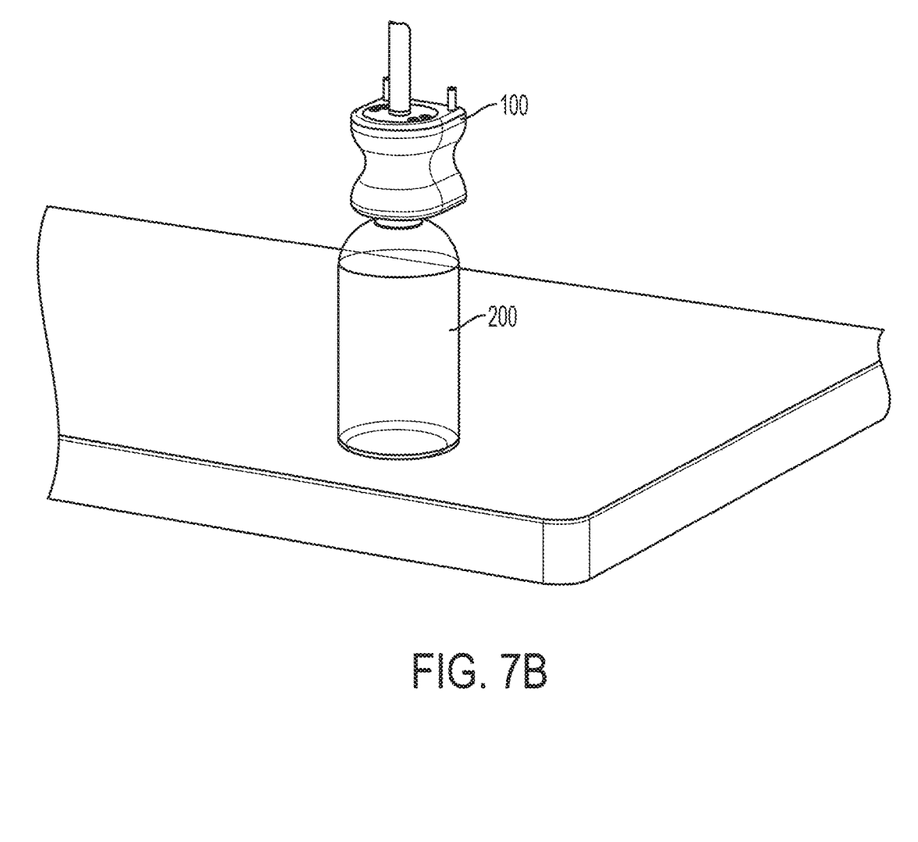
Figure 7C:
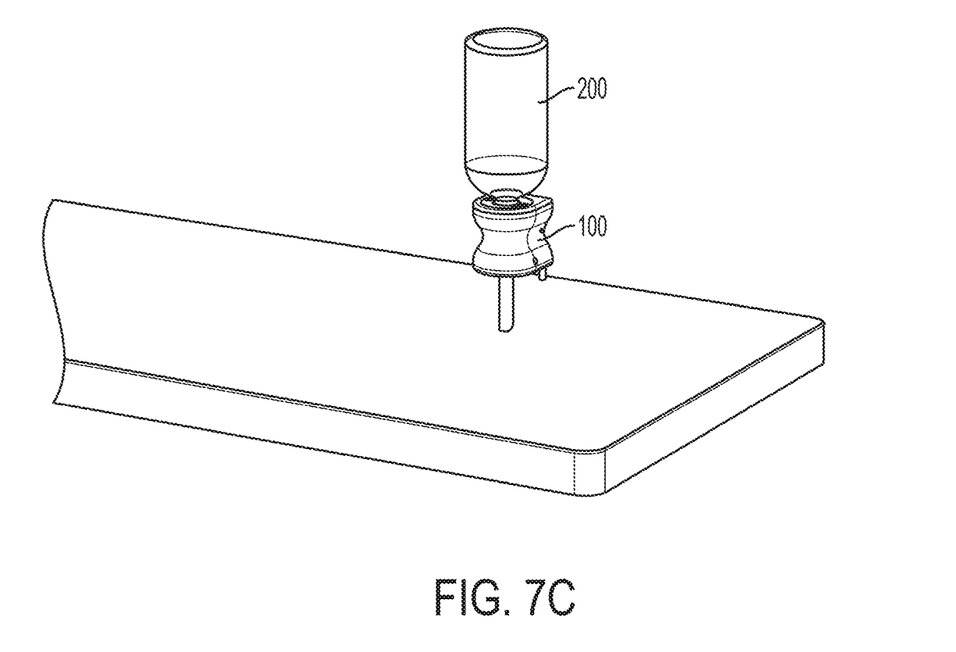
Figure 7D:
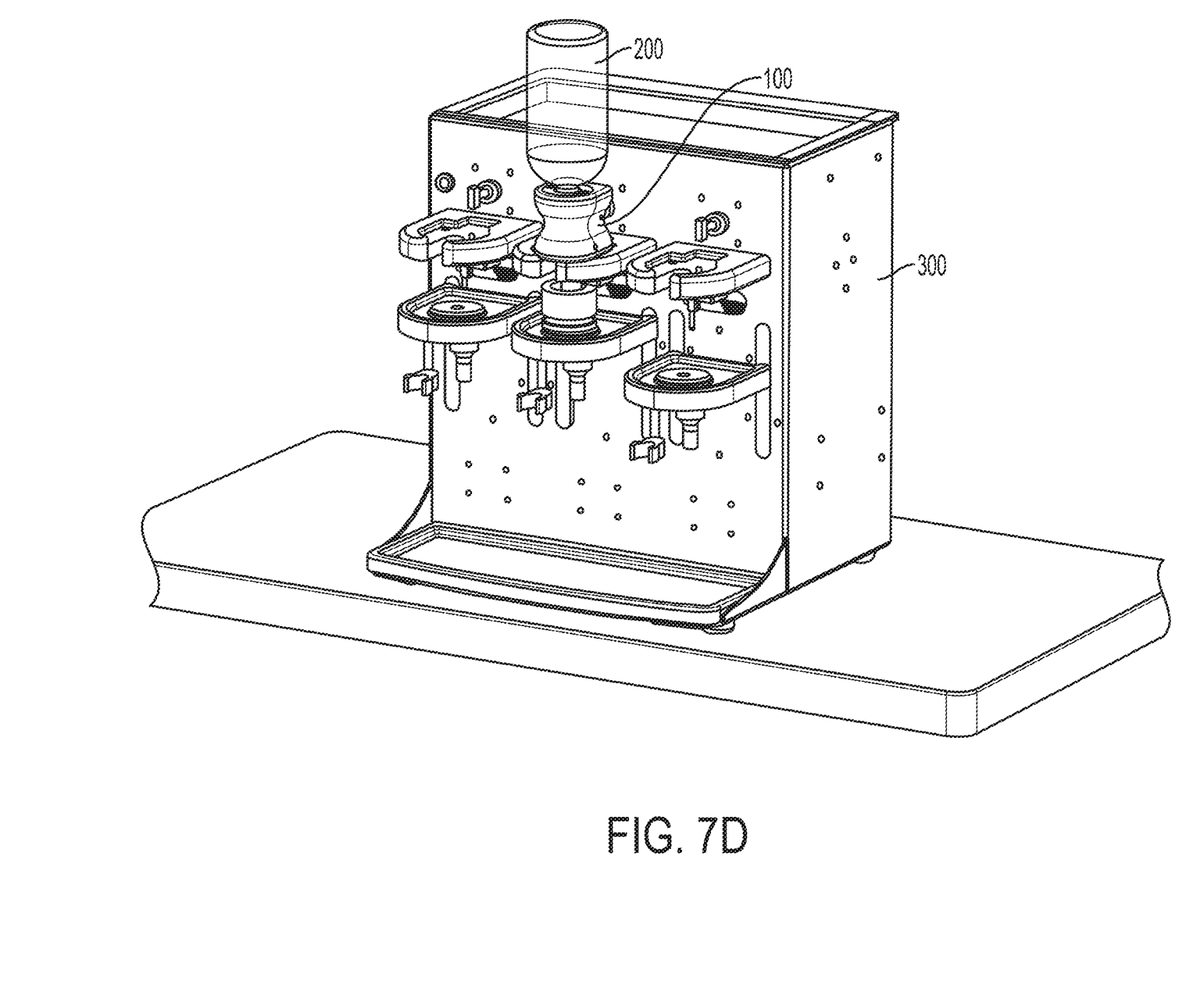

FIGS. 7A-D illustrate a sequence of events for using the liquid inlet device 100. Initially, the liquid inlet device 100 may be inverted, as illustrated in FIG. 7A. Adjacent to the liquid inlet device 100 is a sample bottle 200, shown in an upright position. As illustrated in FIG. 7B, the sample bottle 200 has a threaded portion 210 (see FIG. 6) adapted for coupling with the threaded opening 120a of first insert 120 (see FIG. 2). If necessary, the valve seal 140 is rotated to the closed position, either before or after coupling liquid inlet device 100 with sample bottle 200. The liquid inlet device 100 and sample bottle are inverted so that the sample bottle is upside down (FIG. 7C) and subsequently positioned in a bottle extractor system 300 (FIG. 7D). Since liquid inlet device 100 is screwed onto sample bottle 200 and valve seal 140 is closed, there is no loss of sample when rotating the sample bottle upside down. Notably, downwardly extending tube 130 extends toward chamber 230 and disk 220, port 170 receives pressurized solvent, and stem portion 140b of valve seal 140 seats onto an actuator (not shown) of the bottle extractor system 300. With valve seal 140 remaining in a closed position, pressurized solvent enters through port 170, passes through inlet 167 of nozzle 165, and exits through outlet 169. The solvent contacts closed plug portion 140a (or alternatively closed ball portion) and drips onto disk 220 to condition the disk with solvent. Notably, there is no loss of solvent when conditioning disk 220 when spraying solvent while valve seal 140 is in the closed position. After the disk is conditioned with solvent, pressurized solvent spray is turned off, and the actuator rotates handle portion 140b of valve seal 140 to the open position, allowing liquid in sample bottle 200 to pass through the downwardly extending tube 130 and into chamber 230. As liquid flows out of sample bottle 200, chamber 230 begins to fill. When the liquid level in chamber 230 reaches the bottom of downwardly extending tube 130, flow stops because air cannot pass into the sample bottle and further liquid is prevented from overflowing chamber 230. As liquid flows through disk 220 and liquid level in chamber 230 drops, air passes into sample bottle 220 through tube 130, and additional liquid can pass from sample bottle 200 into chamber 230. Once the bottle is emptied, pressurized solvent is again sprayed through port 170, inlet 167 of nozzle 165, and through outlet 169. Since valve seal 140 is in an open position, solvent exits nozzle 165 at outlet 169 and sprays into sample bottle 200, contacting the base and walls of sample bottle 200. Solvent then flows through downwardly extending tube 130 into chamber 230, ultimately passing through disk 220, which collects dissolved analytes.

Next, the collected solvent extract is furthered processed by the operator.

While this invention has been particularly shown and described with references to example embodiments thereof, it will be understood by those skilled in the art that various changes in form and details may be made therein without departing from the scope of the invention encompassed by the appended claims.

What is claimed is:

1. A method of extracting a sample from a sample bottle, comprising:
   a) coupling a liquid inlet device to the sample bottle, the liquid inlet device comprising:
      i) a housing configured to receive an opening of a sample bottle;
      ii) a valve;
      iii) a nozzle positioned within the housing, the nozzle having an inlet and an outlet, the inlet coupled to a port of the housing; and
      iv) a tube that extends downwardly from the housing;
   b) positioning the liquid inlet device and sample bottle so the tube extends towards a chamber, the port receives pressurized solvent, and the valve couples with an actuator;
   c) spraying solvent through the nozzle with the valve in a closed position so that solvent sprays through the nozzle, against the valve, and through the tube to contact ai a SPE disk;
   d) opening the valve so that a sample in the sample bottle passes through the tube and contacts the SPE disk;
   e) spraying solvent through the nozzle with the valve in an open position so that solvent sprays through the valve to rinse the sample bottle, back through the device, and through the tube.

2. The method of claim 1, wherein the sample is aqueous and the solvent is an organic solvent.

3. The method of claim 1, further comprising inverting the liquid inlet device and sample bottle so that the sample bottle is upside down prior to step b).

4. The method of claim 1, wherein the valve is a plug valve or a ball valve.

5. The method of claim 4, wherein the plug valve or the ball valve has a rotatable seal that couples with the actuator.

6. The method of claim 5, wherein the seal has a stem.

7. The method of claim 1, wherein the valve further comprises a flange portion that ensures a tight fit between the valve and a seat for the valve.

8. The method of claim 1, further comprising a constant force spring and a spanner nut that secure the valve to the housing.

9. The method of claim 1, wherein the housing has a threaded portion configured to receive the opening of the sample bottle.

10. The method of claim 9, further comprising a first insert within the housing, the first insert having the threaded portion configured to receive the opening of the sample bottle.

11. The method of claim 10, further comprising a second insert within the housing, the second insert receiving the nozzle and the tube.

12. The method of claim 1, wherein the nozzle is rotatably adjustable.

13. The method of claim 1, wherein the inlet of the nozzle is oriented at 180° relative to the outlet of the nozzle.

* * * * *

UNITED STATES PATENT AND TRADEMARK OFFICE
CERTIFICATE OF CORRECTION

PATENT NO. : 10,422,730 B2
APPLICATION NO. : 15/700934
DATED : September 24, 2019
INVENTOR(S) : Thomas James Vitella and Robert Stockton Johnson It is certified that error appears in the above-identified patent and that said Letters Patent is hereby corrected as shown below:

In the Claims

Claim 1, Column 5, Line 32, delete "ai" after the word "contact."

Signed and Sealed this
Tenth Day of December, 2019

Andrei Iancu
*Director of the United States Patent and Trademark Office*